(12) United States Patent
Li et al.

(10) Patent No.: US 11,066,377 B2
(45) Date of Patent: *Jul. 20, 2021

(54) PROCESS FOR PRODUCING AROMATIC PRIMARY DIAMINES

(71) Applicant: RHODIA OPERATIONS, Paris (FR)

(72) Inventors: Peng Li, Shanghai (CN); Floryan Decampo, Milan (IT)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,356

(22) Filed: Feb. 4, 2020

(65) Prior Publication Data

US 2020/0172501 A1    Jun. 4, 2020

Related U.S. Application Data

(63) Continuation of application No. 15/324,932, filed as application No. PCT/CN2015/083535 on Jul. 8, 2015, now Pat. No. 10,899,726.

(30) Foreign Application Priority Data

Jul. 10, 2014 (WO) .................. PCT/2014/081945

(51) Int. Cl.
*C07D 307/52* (2006.01)
*C07C 209/26* (2006.01)

(52) U.S. Cl.
CPC .......... *C07D 307/52* (2013.01); *C07C 209/26* (2013.01)

(58) Field of Classification Search
CPC ........................... C07D 307/52; C07C 209/26
See application file for complete search history.

(56) References Cited

U.S. PATENT DOCUMENTS

| | | | |
|---|---|---|---|
| 4,215,073 | A | 7/1980 | Cornils et al. |
| 4,598,159 | A | 7/1986 | Ayusawa et al. |
| 5,041,675 | A | 8/1991 | Lukas et al. |
| 5,055,618 | A | 10/1991 | Kampmann et al. |
| 2007/0232833 | A1 | 10/2007 | Haese et al. |
| 2008/0167499 | A1 | 7/2008 | Molitor et al. |
| 2010/0222611 | A1 | 9/2010 | Tulchinsky et al. |

FOREIGN PATENT DOCUMENTS

| | | |
|---|---|---|
| JP | S60-146885 A | 8/1985 |
| JP | S62-446 A | 1/1987 |
| JP | H10-130210 A | 5/1998 |
| JP | 2010-513302 A | 4/2010 |
| WO | 2012/004069 A1 | 1/2012 |

*Primary Examiner* — John Mabry
(74) *Attorney, Agent, or Firm* — Osha Bergman Watanabe & Burton LLP

(57) ABSTRACT

The present disclosure relates to a process for the production of aromatic primary amines, by reacting an aromatic dialdehyde with hydrogen and ammonia or an ammonia-liberating compound, in the presence of a hydrogenation catalyst and an amine, wherein the molar ratio of the amine to the aromatic dialdehyde is no less than 1:4 at the start of the reaction.

20 Claims, No Drawings

PROCESS FOR PRODUCING AROMATIC PRIMARY DIAMINES

This application is a continuation of U.S. application Ser. No. 15/324,932, filed Jan. 9, 2017, which is a U.S. national phase entry under 35 U.S.C. § 371 of International Application No. PCT/CN2015/083535, filed on Jul. 8, 2015, which claims priority to PCT International Application No. PCT/CN2014/081945, filed on Jul. 10, 2014. The entire contents of these applications are explicitly incorporated herein by this reference.

TECHNICAL FIELD

The present invention relates to a process for producing aromatic primary diamines by reductive amination of their corresponding aromatic dialdehydes.

BACKGROUND ART

Several processes were known for producing primary diamines from reductive amination of the corresponding dialdehydes, with ammonia and hydrogen and in the presence of a hydrogenation catalyst.

U.S. Pat. No. 2,636,051 A (SHELL DEV) Apr. 21, 1953 discloses a process for preparing long-chain aliphatic primary diamines upon conversion of aliphatic dialdehydes wherein the formyl groups are separated by at least four carbon atoms, by feeding the aliphatic dialdehyde to a reactor containing ammonia, hydrogen and a hydrogenation catalyst at a controlled flow rate, and provided an example with 60% yield of the primary diamine product using a Raney nickel catalyst and water solvent.

In a couple of later published patents, such as JP 05-017413 A (KOEI CHEM CO LTD) Jan. 26, 1993, JP 07-069999 (CHEM LINZ AG) Mar. 14, 1995, JP 07-196586 A (KURARY CO LTD) Aug. 1, 1995, JP 10-130210 A (KURARAY CO LTD) May 19, 1998, JP 10-310559 A (KURARAY CO LTD) Nov. 24, 1998, and U.S. Pat. No. 6,696,609 (KURARAY CO. LTD) Apr. 3, 2003, modified processes for preparing aliphatic primary diamines (e.g. 1,8-octanediamine, 1,9-nonanediamine, and 2-methyl-1,8-octanediamine) were suggested, each using at least one organic solvent replacing the water solvent applied in U.S. Pat. No. 2,636,051 for a higher diamine product yield (86.9% to 96%). These organic solvents include: alcoholic solvents such as methanol or ethanol; aromatic hydrocarbon such as toluene; and ether solvents such as tetrahydrofuran, 1,4-dioxane, and methyl-t-butyl ether. Of these organic solvents, U.S. Pat. No. 6,696,609 (KURARAY CO. LTD) Apr. 3, 2003 suggested the preference on methanol or ethanol, and emphasized that the proportion of primary amine in the reaction mixture should be minimized, in order to produce the desired aliphatic diamines (i.e. 1,9-nonanediamine and 2-methyl-1,8-octanediamine) with a high yield of above 90%.

However, according to a follow-up test conducted by the present inventors (see Comparative Example 1), the general amination reaction system used in the above mentioned patents for converting alphatic dialdehydes is not effective, or rather inapplicable, for reductive amination of aromatic dialdehydes. In fact, using the same Experimental protocol of U.S. Pat. No. 6,696,600, the latest published patent application among the above mentioned patents, massive precipitation formed in the reaction system for converting 2,5-diformylfuran (DFF) and no primary diamine product was detected.

In view of the shortcomings of the above-discussed prior art, it is an object of the present invention to provide an effective process for preparing aromatic primary diamines from the corresponding aromatic dialdehydes, at a high yield and an economical cost.

Surprisingly and unexpectedly, this object is achieved by the present invention using a new process to prepare aromatic primary diamine by reductive amination of its corresponding dialdehyde, which does not diminish amine presence in the reaction mixture but rather keeps a minimal amine/dialdehyde ratio at the start of the reaction, in order to increase the product yield.

SUMMARY OF INVENTION

The present invention provides a process for the production of an aromatic primary amine, the process comprising reacting an aromatic dialdehyde with hydrogen and ammonia or an ammonia-liberating compound, in the presence of a hydrogenation catalyst and an amine, wherein the molar ratio of the amine to the aromatic dialdehyde is no less than 1:4 at the start of the reaction.

According to the process of the present invention, by keeping a minimal amine/dialdehyde ratio at the start of the reaction, aromatic primary diamine can be produced in high yields and at an economical cost. This effect, which is a new finding of the present inventors, is contrary to the prior art teaching on the suppression of primary amine in the reaction mixture to favour the intended reductive amination. Furthermore, the present process can be readily adapted for batch or continuous operation mode, thus applicable to a wide range of industrial applications.

This application claims priority to PCT application No. PCT/CN2014/081945, the whole content of this application being incorporated herein by reference for all purposes.

The term "amine", as used herein, refers to an organic compound derived by replacing one or more of the hydrogen atoms in ammonia by an organic group, and includes primary, secondary and tertiary amines. Preferably, the amine used at the start of the reaction in the present process is a primary amine or a secondary amine, more preferably a primary amine.

According to the present invention, a "primary amine" is a compound of the formula $RNH_2$, a "secondary amine" is a compound of the formula HNRR', and a "tertiary amine" is a compound of the formula NRR'R", wherein R, R', R" are each independently an organic radical. The term "aromatic primary amine", as used herein, refers to an aromatic compound which is also a primary amine.

Unlimited examples of R, R' and R" may be independently selected from the group consisting of alkyl, cycloalkyl, aryl, heterocyclyl, heteroaryl, alkylcycloalkyl, alkylaryl, alkylheterocyclyl, alkylheteroaryl, and alkoxyalkyl. Preferably, R, R' and R" are independently selected from a group consisting of straight or branched (C1-C10) alkyl, phenyl (C1-C3) alkyl, and heteroaryl (C1-C3) alkyl, each optionally substituted with substituents selected from the group consisting of halogen, hydroxy, alkoxy, amino, nitro, halogen, cycloalkyl, and alkyl.

In some embodiments of the present process invention, the amine used at the start of the reaction is a primary amine.

Specific examples of primary amines used at the start of the reaction of the present process include methylamine, ethylamine, propylamine, butylamine, pentylamine, hexylamine, benzylamine, cyclohexylamine, ethylene diamine and the like. Preferred primary amine examples notably include methylamine, butylamine, pentylamine, and hexylamine, of which methylamine and butylamine are further preferred. Advantageously, it is found that butylamine generally gives a vapour pressure high enough at low temperatures in the reaction system, thus permits easy recovery.

Notably, aromatic diamines obtainable from the present process are also usable as the amine ingredient at the start of the reaction.

Alternatively, the amine used at the start of the reaction in the present process is a secondary amine of the formula HNRR', wherein R and R' are as defined above.

As another alternative, the amine used at the start of the reaction in the present process is a tertiary amine of the formula NRR'R", wherein R, R' and R" are as defined above.

Exemplified secondary amines used at the start of the reaction of the present process include dimethylamine, diethylamine, diethanolamine, dicyclohexylamine, diallylamine, piperidine, pyrolidine, morpholine, N-methylbenzylamine, dibenzylamine and the like. Preferred secondary amines used in the present invention include dimethylamine, diethylamine, and N-methylbenzylamine.

Exemplified tertiary amines used in the reaction of the present process include trimethylamine, triethylamine, triethanolamine, diisopropylethylamine, tricyclohexylamine, triallylamine, benzyldimethylamine, N-methylmorpholine, N-methyldibenzylamine and the like. Preferred tertiary amines used in the present invention include trimethylamine, triethylamine, and benzyldimethylamine.

As used in the present invention, the term "aromatic dialdehyde" refers to a compound having at least one aromatic ring substituted with two aldehyde groups. The aromatic ring as used herein can be a hydrocarbon or heterocyclic ring, and may be selected from a group consisting of benzene, pyrene, furan, thiophene, terthiophene, pyrrole, pyridine, terpyridine, pyridine oxide, pyrazine, indole, quinoline, purine, quinazoline, bipyridine, phenanthroline, naphthalene, tetralin, biphenyl, cyclohexylbenzene, indan, anthracene, phenanthrene, fluorene, and azulene, each being optionally substituted with at least one substitution selected from a group consisting of $C_1$-$C_{24}$ alkyl, amino, hydroxyl, carboxyl, ester, cyano, nitro, halogen, and oxygen.

Particularly preferred examples of the aromatic dialdehyde used in the invention include those having at least one furan ring substituted with two aldehyde groups, such as 2,5-diformylfuran (DFF) and its derivatives.

Other examples of the aromatic dialdehyde used in the invention include, notably, phthalaldehyde; isophthalaldehyde; terephthalaldehyde; 1,2-naphthalenedicarboxaldehyde; 1,3-naphthalenedicarboxaldehyde; 1,4-naphthalenedicarboxaldehyde; 1,6-naphthalenedicarboxaldehyde; 1,8-naphthalenedicarboxaldehyde; 2,6-naphthalenedicarboxaldehyde; 1,7-naphthalenedicarboxaldehyde; 2,5-naphthalenedicarboxaldehyde; 1,4-anthracenedicarboxaldehyde; 1,6-anthracenedicarboxaldehyde; 1,10-anthracenedicarboxaldehyde; 2,3-anthracenedicarboxaldehyde; 2,7-anthracenedicarboxaldehyde; 1,2-anthracenedicarboxaldehyde; 1,9-anthracenedicarboxaldhyde; 9,10-anthracenedicarboxaldehyde; 1,2-phenanthrenedicarboxaldehyde; 1,4-phenanthrenedicarboxaldehyde; 1,9-phenanthrenedicarboxaldehyde; 2,3-phenanthrenedicarboxaldehyde; 3,5-phenanthrenedicarboxaldehyde; 9,10-phenanthrenedicarboxaldehyde; 4,4'-biphenyldicarboxaldehyde; 3,3-biphenyldicarboxaldehyde; 2,3-biphenyldicarboxaldehyde; 2,4-biphenyldicarboxaldehyde; 2,6-biphenyldicarboxaldehyde; 2,2"-(p-terphenyl) dicarboxaldehyde; 2,3-(o-terphenyl) dicarboxaldehyde; 2,6'-(m-terphenyl) dicarboxaldehyde; 1,4'-(o-terphenyl) dicarboxaldehyde; 4,4"-(p-terphenyl) dicarboxaldehyde; 3,3'-(p-terphenyl) dicarboxaldehyde; 2,6-(o-terphenyl) dicarboxaldehyde; and the like.

The above mentioned aromatic dialdehydes are known in the art and can be readily prepared by, for example, hydrolysis of dihalides, Gattermanns carbon monoxide synthesis using formyl chloride or the equivalent thereof, and oxidation of various aromatic materials.

The present process requires that, at the start of the amination reaction, the molar ratio of the amine to the aromatic dialdehyde is no less than 1:4, preferably no less than 1:2, and more preferably no less than 1:1.

Also preferably, at the start of the amination reaction, the molar ratio of the amine to the aromatic dialdehyde is no more than 4:1, preferably no more than 3:1, and more preferably no more than 2:1. At the start of the amination reaction, the molar ratio of the amine to the aromatic dialdehyde may be then comprised between 1:4 and 4:1, more preferably comprised between 1:2 and 4:1 (limit inclusive).

Without wishing to be bound to any particular theory, it is believed that the aromatic dialdehyde reactant was first reacted with amine to form a diimine intermediate, which is then hydrogenated in the presence of ammonia to form the diamine product in the reaction system.

In the process of the present invention, ammonia or an ammonia-liberating compound or mixtures thereof may be used. Examples of such ammonia-liberating compounds include urea, uric acid, ammonium salts and derivatives of a primary amide, for example, symmetrical and unsymmetrical carbamates, carbaminates, semicarbazides and semicarbazoles, or aminium salts or organic/inorganic esters thereof. Preference may be given to using ammonia itself, with liquid or gaseous ammonia being able to be used in this embodiment.

As the preferred molar ratio of the aromatic dialdehyde to the equivalents of ammonia, which may be formed from the ammonia introduced and/or the ammonia-liberating compound or the sum of such compounds used in the process, value in the range of 1:2-1:50 and preferably in the range of 1:5-1:20 may be set.

The hydrogenation catalyst usable for the present process may be selected from Raney catalysts such as Raney nickel, Raney cobalt and Raney copper. Alternatively, said hydrogenation catalyst may be selected from supported catalysts comprising a metal having hydrogenation activity such as nickel, cobalt, platinum, palladium, rhodium, ruthenium or copper on a support such as Kieselguhr, silica, alumina, silica-alumina, clay, titania, zirconia, magnesia, calcia, lanthanum oxide, niobium oxide or carbon. These hydrogenation catalysts may have any shape such as powder, grains or pellets. The amount of the hydrogenation catalyst used may vary according to the desired reaction rate, and it is desirably in a range of 0.01 to 30% by weight based on the weight of the reaction mixture, more preferably in a range of 0.1 to 10% by weight on the same basis. The hydrogenation catalyst may be used in the form of suspension or as a fixed bed. Nickel hydrogenation catalysts include those commercially available under the trade designations "PRICAT 9908", "PRICAT 9910", "PRICAT 9920", "PRICAT 9932", "PRICAT 9936," "PRICAT 9939", "PRICAT 9953", "PRICAT 20/15 D", "PRICAT NI 52/35", "PRICAT NI 52/35 P", "PRICAT NI 55/5 P", "PRICAT NI 60/15 P", "PRICAT NI 62/15 P", "PRICAT NI 52/35 T", "PRICAT NI 55/5 T" and "PRICAT NI 60/15 T" (available from Johnson Matthey Catalysts, Ward Hill, Mass.) (wherein D=droplet, P=powder, and T=tablet). Hydrogenation catalyst may also be chosen from nickel catalysts such as Ni/PrO2-CeO2 catalysts and CuNiOx catalysts, optionally comprising another metal such as Zn or Pd for instance.

Although not specifically limited, the amination reaction of the present process is desirably carried out under a hydrogen partial pressure in a range of 0.1 to 25 MPa, and more preferably in a range of 0.5 to 20 MPa. Optionally, hydrogen may be added during the reaction to make up for the consumption or continuously circulated through the reaction zone.

Preferably, the amination reaction of the present process is carried out in a liquid phase using a solvent. The solvent used should be liquid under the temperature and pressure throughout the amination reaction, and substantially inert to the reactants and products in the reaction mixture of the present process. Suitable examples of such solvent include: alcoholic solvent such as methanol, ethanol, 2-propanol, 1-butanol, isoamyl alcohol and n-octyl alcohol; an aromatic hydrocarbon solvent such as toluene; or an ether solvent such as methyl t-butyl ether, tetrahydrofuran and 1,4-dioxane, among which methanol and ethanol are preferred.

These solvents may be used in any amount with no specific restrictions, but desirably in an amount ranging from 0.5 to 50 times the weight of the aromatic dialdehyde used, and more preferably in an amount of 2 to 10 times the weight of the aromatic dialdehyde used.

The reaction temperature is desirably in a range of 40 to 200° C., more preferably in a range of 100 to 150° C.

The reaction can be carried out either batchwise or continuously. In either case, it is recommended to feed the aromatic dialdehyde in a manner to ensure that the molar ratio of amine to the aromatic dialdehyde is no less than 1:4 throughout the reaction, and is preferably in a range of 1:4 to 2:1, more preferably in a range of 1:1 to 2:1.

Suitable reaction vessels for carrying out the amination reaction of the present process may be selected from conventional types of autoclaves and conventional types of tubular reactors. Depending on the specific medium and/or depending on the specific conditions of the respective reaction, the reactor may be operated under the atmospheric pressure or under a partial pressure of 0.1-20 MPa, preferably 0.5-10 MPa and more preferably 1-3 MPa. This pressure may be generated by injected hydrogen and ammonia and/or by pressurization of the reactor with a further, preferably inert gas such as nitrogen or argon and/or by formation of ammonia in situ from an ammonia-liberating compound or mixtures thereof and/or by setting of the desired reaction temperature.

In the present process, the sequence of adding different reactants is not strictly limited. In one embodiment of the reaction, an aromatic dialdehyde or its solution in a solvent is fed together with ammonia to a reaction vessel filled with a hydrogenation catalyst, amine, a solvent and hydrogen. In an alternative embodiment, hydrogen was introduced in a reaction vessel containing a premix of an aromatic dialdehyde, amine, ammonia and a hydrogenation catalyst in a solvent. In yet another embodiment, the aromatic dialdehyde is dropwise added to a reaction vessel containing a premix of an amine, ammonia, hydrogen and hydrogenation catalyst in a solvent.

The amination reaction of the present process gives an aromatic diamine corresponding to the dialdehyde used, e.g. 2,5-bis(aminomethyl)furan (FDA) obtained from DFF: p-xylylenediamine from terephthalaldehyde; m-xylylenediamine from isophthalaldehyde and bis(5-amino-2-furfuryl) ether from bis(5-formyl-2-furfuryl)ether.

Of the above mentioned aromatic diamine products, the DFF-converted FDA is of particular interest, since FDA is a frequently used starting material in polyamine, polyamide and polyurethane syntheses, while DFF is widely available from biomass-derived resources.

The aromatic diamine obtained from the amination reaction can be purified to a high purity by the usual purification procedure comprising distilling off ammonia and any present solvent from the reaction mixture from which the hydrogenation catalyst has been separated and subjecting the residue to distillation or recrystallization.

DESCRIPTION OF EMBODIMENTS

Having generally described the invention, a further understanding may be obtained by reference to the examples below, which are provided for the sole purpose of illustration and not intending to limit the invention. Should the disclosure of any patents, patent applications, and publications which are incorporated herein by reference conflict with the description of the present application to the extent that it may render a term unclear, the present description shall take precedence

EXAMPLES

Example 1

To a 100 mL Parr reactor containing 200 mg Raney Co, 2.0 mmol DFF and 6.0 mmol N-butylamine was introduced with 25 mL ethanol. The reactor was then purged with nitrogen for three times, and the mixture was agitated under an ammonia atmosphere (0.2 MPa) to dissolve approximately 2 g of ammonia in the alcohol. Hydrogen was then introduced into the reactor to provide a hydrogen partial pressure of 2 MPa, and the reaction then proceeded at a temperature of 150° C. for 3 hours. After completion of the reaction, the reactor was allowed to cool down and unreacted ammonia was released. Analysis of the residual liquid phase in the reactor by gas chromatography revealed that 112 mg of FDA was obtained, giving a yield of 44% based on the DFF used.

Comparative Example 1

Example 1 of U.S. Pat. No. 6,696,609 was reproduced in this Comparative Example, with identical experimental conditions to supress the generation of primary amine in the reaction system.

A 100 ml Parr reactor equipped with a mechanical stirrer was charged with 25 ml of methanol and 150 mg of Raney nickel. After being flushed for three times with nitrogen, the autoclave was then charged with 2 g of ammonia and, while a hydrogen partial pressure of 3 MPa was applied, heated to a temperature of 140° C. Thereafter, a methanolic solution obtained by dissolving 620 mg (5 mmol) of DFF in 25 ml of methanol was fed through a high-pressure metering pump to the autoclave over 1 hour. After completion of the feeding, the reaction mixture was stirred for another 1 hour at 140° C. Massive charcoal-like precipitate was observed to form in the reactor and the GC-MS analysis of the residual solution showed that no aminated product was formed.

Example 2

To a 100 mL Parr reactor containing 200 mg Raney Co, 2.0 mmol DFF and 6.0 mmol methylamine (in the form of a 40 wt % aqueous solution) was introduced with 25 mL methanol. The reactor was then purged with nitrogen for three times, and the mixture was agitated under an ammonia atmosphere (0.2 MPa) to dissolve approximately 2 g of ammonia in the alcohol. Hydrogen was then introduced into the reactor to provide a hydrogen partial pressure of 2 MPa, and the reaction then proceeded at a temperature of 115-120° C. for 3 hours. After completion of the reaction, the reactor was allowed to cool down and unreacted ammonia was released. Analysis of the residual liquid phase in the reactor by gas chromatography revealed that 97 mg of FDA was obtained, giving a yield of 33% based on the DFF used.

Comparative Example 3

The operation of Example 1 was repeated in the absence n-butylamine, there was obtained only 18 mg of FDA, corresponding to a yield of 7% based upon the DFF used.

Comparative Example 4

The operation of Example 1 was repeated expect that 0.4 mmol n-butylamine was introduced into the mixture of Raney Co and DFF. There was obtained 63 mg of FDA, corresponding to a yield of 25% based upon the DFF used.

Example 5

The operation of Example 1 was repeated, expect that 2.0 mmol n-butylamine was introduced into the mixture of Raney Co and DFF. There was obtained 96 mg of FDA, corresponding to a yield of 38% based upon the DFF used.

Example 6

To a 100 mL Parr reactor containing 120 mg Pricat Ni 52/35, 2.0 mmol DFF and 6.0 mmol n-butylamine was introduced 25 mL methanol. The reactor was then purged with nitrogen for three times, and the mixture was agitated under an atmosphere of 0.2 MPa ammonia to dissolve approximately 2 g of ammonia in the alcohol. Hydrogen was then introduced into the reactor to provide a hydrogen partial pressure of 2 MPa, and the reaction then proceeded at a temperature of 115-120° C. for 4 hours. After completion of the reaction, the reactor was allowed to cool down and unreacted ammonia was released. Analysis of the residual liquid phase in the reactor by gas chromatography revealed that 55 mg of FDA and 44 mg of tertahydrofuran-2,5-dimethylamine (THFDA) were obtained. the yields based on the DFF used are 22% and 17% respectively.

Example 7

To a 100 mL Parr reactor containing 120 mg of a Ni/PrO2-CeO2 catalyst, 2.0 mmol DFF and 6.0 mmol n-butylamine was introduced 25 mL methanol. The reactor was then purged with nitrogen for three times, and the mixture was agitated under an atmosphere of 0.2 MPa ammonia to dissolve approximately 2 g of ammonia in the alcohol. Hydrogen was then introduced into the reactor to provide a hydrogen partial pressure of 2 MPa, and the reaction then proceeded at a temperature of 115-120° C. for 4 hours. After completion of the reaction, the reactor was allowed to cool down and unreacted ammonia was released. Analysis of the residual liquid phase in the reactor by gas chromatography revealed that 114 mg of FDA was obtained, giving a yield of 45% based on the DFF.

Example 8

To a 100 mL Parr reactor containing 120 mg of a CuNiOx catalyst, 2.0 mmol DFF and 6.0 mmol n-butylamine was introduced 25 mL methanol. The reactor was then purged with nitrogen for three times, and the mixture was agitated under an atmosphere of 0.2 MPa ammonia to dissolve approximately 2 g of ammonia in the alcohol. Hydrogen was then introduced into the reactor to provide a hydrogen partial pressure of 2 MPa, and the reaction then proceeded at a temperature of 115-120° C. for 4 hours. After completion of the reaction, the reactor was allowed to cool down and unreacted ammonia was released. Analysis of the residual liquid phase in the reactor by gas chromatography revealed that 124 mg of FDA was obtained, giving a yield of 49% based on the DFF.

Example 9

To a 100 mL Parr reactor containing 120 mg of a CuNiOx catalyst, 2.0 mmol DFF and 6.0 mmol n-butylamine was introduced 25 mL methanol. The reactor was then purged with nitrogen for three times, and the mixture was agitated under an atmosphere of 0.2 MPa ammonia to dissolve approximately 2 g of ammonia in the alcohol. Hydrogen was then introduced into the reactor to provide a hydrogen partial pressure of 2 MPa, and the reaction then proceeded at a temperature of 80° C. for 15 hours. After completion of the reaction, the reactor was allowed to cool down and unreacted ammonia was released. Analysis of the residual liquid phase in the reactor by gas chromatography revealed that 211 mg of FDA was obtained, giving a yield of 84% based on the DFF.

The invention claimed is:

1. A process for the production of an aromatic primary diamine, the process comprising reacting an aromatic dialdehyde, wherein the aromatic ring is a hydrocarbon ring, with hydrogen and ammonia or an ammonia-liberating compound selected from the group consisting of urea, uric acid, ammonium salts, symmetrical and unsymmetrical carbamates, carbaminates, semicarbazides, semicarbazoles, and aminium salts and organic/inorganic esters thereof, in the presence of a hydrogenation catalyst and an amine, wherein the molar ratio of the amine to the aromatic dialdehyde is no less than 1:4 at the start of the reaction.

2. The process of claim 1, wherein the amine is selected from a group consisting of methylamine, ethylamine, propylamine, butylamine, pentylamine, hexylamine, benzylamine, cyclohexylamine, ethylene diamine, dimethylamine, diethylamine, diethanolamine, dicyclohexylamine, diallylamine, piperidine, pyrolidine, morpholine, N-methylbenzylamine, dibenzylamine, trimethylamine, triethylamine, triethanolamine, diisopropylethylamine, tricyclohexylamine, triallylamine, benzyldimethylamine, N-methylmorpholine, and N-methyldibenzylamine.

3. The process of claim 1, wherein the aromatic ring is benzene.

4. The process of claim 1, wherein the aromatic diamine is m-xylylenediamine and the aromatic dialdehyde is isophthalaldehyde.

5. The process of claim 4, wherein the amine is a primary amine or a secondary amine.

6. The process of claim 5, wherein the amine is a primary amine.

7. The process of claim 6, wherein the primary amine is selected from a group consisting of methylamine, ethylamine, propylamine, butylamine, pentylamine, hexylamine, benzylamine, cyclohexylamine, and ethylene diamine.

8. The process of claim 4, wherein the amine is a secondary amine selected from the group consisting of dimethylamine, diethylamine, diethanolamine, dicyclohexylamine, diallylamine, piperidine, pyrolidine, morpholine, N-methylbenzylamine, and dibenzylamine.

9. The process of claim 4, wherein the amine is a tertiary amine selected from a group consisting of trimethylamine, triethylamine, triethanolamine, diisopropylethylamine, tricyclohexylamine, triallylamine, benzyldimethylamine, N-methylmorpholine, and N-methyldibenzylamine.

10. The process of claim 4, wherein the molar ratio of the amine to isophthalaldehyde is no less than 1:1, at the start of the reaction.

11. The process of claim 4, wherein the molar ratio of the amine to isophthalaldehyde is no more than 3:1 at the start of the reaction.

12. The process of claim 4, wherein the molar ratio of isophthalaldehyde to the equivalents of ammonia is in the range of 1:5-1:20.

13. The process of claim 4, wherein isophthalaldehyde is fed in a manner to ensure that the molar ratio of amine to isophthalaldehyde is in a range of 1:4 to 2:1.

14. The process of claim 4, wherein the hydrogenation catalyst is Raney copper, $Ni/PrO_2-CeO_2$, or CuNiOx, optionally comprising another metal Zn or Pd.

15. The process of claim 4, wherein ammonia is used.

16. The process of claim 1, wherein the aromatic diamine is p-xylylenediamine and the aromatic dialdehyde is terephthalaldehyde.

17. The process of claim 16, wherein the amine is a primary amine selected from a group consisting of methylamine, ethylamine, propylamine, butylamine, pentylamine, hexylamine, benzylamine, cyclohexylamine, and ethylene diamine.

18. The process of claim 16, wherein the amine is a secondary amine selected from the group consisting of dimethylamine, diethylamine, diethanolamine, dicyclohexylamine, diallylamine, piperidine, pyrolidine, morpholine, N-methylbenzylamine, and dibenzylamine.

19. The process of claim 16, wherein the amine is a tertiary amine selected from a group consisting of trimethylamine, triethylamine, triethanolamine, diisopropylethylamine, tricyclohexylamine, triallylamine, benzyldimethylamine, N-methylmorpholine, and N-methyldibenzylamine.

20. The process of claim 16, wherein the molar ratio of the amine to terephthalaldehyde is no less than 1:1, at the start of the reaction.

* * * * *